(12) United States Patent
Choi et al.

(10) Patent No.: US 9,764,053 B2
(45) Date of Patent: Sep. 19, 2017

(54) SCENT DIFFUSER AND CLOTHES TREATMENT APPARATUS INCLUDING THE SAME

(71) Applicant: LG ELECTRONICS INC., Seoul (KR)

(72) Inventors: Junyoung Choi, Seoul (KR); Youngjin Doh, Seoul (KR); Wansik Nam, Seoul (KR)

(73) Assignee: LG Electronics Inc., Seoul (KR)

(*) Notice: Subject to any disclaimer, the term of this patent is extended or adjusted under 35 U.S.C. 154(b) by 0 days.

(21) Appl. No.: 14/974,078

(22) Filed: Dec. 18, 2015

(65) Prior Publication Data

US 2016/0175471 A1    Jun. 23, 2016

(30) Foreign Application Priority Data

Dec. 19, 2014 (KR) .................. 10-2014-0184786

(51) Int. Cl.
*A61L 9/12* (2006.01)
*D06F 58/10* (2006.01)
*D06F 73/02* (2006.01)
*D06F 58/20* (2006.01)

(52) U.S. Cl.
CPC ............... *A61L 9/12* (2013.01); *D06F 58/10* (2013.01); *D06F 58/203* (2013.01); *D06F 73/02* (2013.01)

(58) Field of Classification Search
None
See application file for complete search history.

(56) References Cited

U.S. PATENT DOCUMENTS

| | | | |
|---|---|---|---|
| 5,004,138 A * | 4/1991 | Gabas | A61L 9/12 224/312 |
| 2005/0050762 A1* | 3/2005 | Hood | D06F 58/203 34/595 |
| 2009/0307924 A1 | 12/2009 | Aouad et al. | |

(Continued)

FOREIGN PATENT DOCUMENTS

| | | |
|---|---|---|
| CN | 2745983 | 12/2005 |
| CN | 201172761 | 12/2008 |
| DE | 7935996 | 6/1980 |

(Continued)

OTHER PUBLICATIONS

Extended European Search Report issued in European Application No. 15201275.3 on Apr. 4, 2016, 10 pages.

(Continued)

*Primary Examiner* — Michael Barr
*Assistant Examiner* — Cristi Tate-Sims
(74) *Attorney, Agent, or Firm* — Fish & Richardson P.C.

(57) ABSTRACT

A scent diffuser includes a holder configured to hold a replaceable scent member, the holder having at least one discharge port configured to discharge scent emitted from the scent member. The scent diffuser further includes a slider with a manipulation part accessible to a user, the slider being configured to move relative to the holder based on force applied by the user to the manipulation part, and the manipulation part being configured to transmit force to the slider, thereby causing the slider to move. The slider is configured to adjust an extent of an opening of the discharge port based on a position to which the slider is moved.

15 Claims, 13 Drawing Sheets

(56) References Cited

U.S. PATENT DOCUMENTS

2010/0011606 A1    1/2010  Kim et al.
2012/0160269 A1*  6/2012  Pyo ...................... D06F 58/203
                                                             134/18

FOREIGN PATENT DOCUMENTS

| | | | | |
|---|---|---|---|---|
| DE | 10318486 | | 10/2004 | |
| EP | 0271453 | | 6/1988 | |
| EP | 2431516 | | 3/2012 | |
| EP | 2657391 | | 10/2013 | |
| KR | 20-0122599 | | 6/1997 | |
| KR | 1997-020884 U | * | 6/1997 | ............. A61L 9/015 |
| KR | 20-0190868 | | 8/2000 | |
| KR | 10-2005-0119297 | | 12/2005 | |
| KR | 10-2011-0043250 | | 4/2011 | |
| KR | 1020110043250 A | * | 4/2011 | ............. D06F 58/10 |
| KR | 10-2014-0016093 | | 2/2014 | |
| KR | 20-0472951 | | 5/2014 | |
| KR | 2020130000085 | * | 5/2014 | ............. D06F 58/20 |
| WO | 2011/126318 | | 10/2011 | |

OTHER PUBLICATIONS

International Search Report in International Application No. PCT/KR2015/014013, mailed Apr. 25, 2016, 3 pages.

* cited by examiner

SCENT DIFFUSER AND CLOTHES TREATMENT APPARATUS INCLUDING THE SAME

CROSS-REFERENCE TO RELATED APPLICATION

This application claims the priority benefit of Korean Patent Application No. 10-2014-0184786, filed on Dec. 19, 2014 in the Korean Intellectual Property Office, the disclosure of which is incorporated herein by reference.

FIELD

The present disclosure relates to a scent diffuser and a clothes treatment apparatus including the same.

BACKGROUND

A clothes treatment apparatus is an apparatus that is used to treat clothes, e.g., wash and dry clothes and smooth wrinkles in clothes. A clothes treatment apparatus may be used at a home or at a laundromat.

There are different classifications of clothes treatment apparatuses, these classifications may include a washer, a dryer, a washer/dryer, a refresher, and a steamer. A washer may be used for washing clothes, a dryer may be used for drying clothes, a washer/dryer may have both a washing and a drying function, a refresher may be used to refresh clothes, and a steamer may be used to remove wrinkles from clothes.

In more detail, a refresher is an apparatus that may be used to keep clothes comfortable and fresh. The refresher may be used to dry clothes, to supply fragrance to clothes, to prevent the occurrence of static electricity in clothes, or to remove wrinkles from clothes.

A steamer is an apparatus that may be used to supply steam to clothes to remove wrinkles from the clothes. Unlike a general iron, the steamer removes wrinkles from the clothes without directly applying heat to the clothes.

A clothes treatment apparatus that includes both functions of a refresher and a steamer may remove wrinkles from clothes received in the clothes treatment apparatus, and may additionally deodorize the clothes, using steam and hot air.

A scent diffuser configured to diffuse scent into a treatment chamber, in which clothes are received, may be used in a clothes treatment apparatus.

SUMMARY

The present disclosure is directed to a scent diffuser that is capable of enabling a user to adjust the amount or concentration of scent to be discharged, and a clothes treatment apparatus including the same.

According to an innovative aspect of the subject matter described in this application, a scent diffuser includes a holder configured to hold a replaceable scent member, the holder having at least one discharge port configured to discharge scent emitted from the scent member; and a slider with a manipulation part accessible to a user, the slider being configured to move relative to the holder based on force applied by the user to the manipulation part, and the manipulation part being configured to transmit force to the slider, thereby causing the slider to move, where the slider is configured to adjust an extent of an opening of the discharge port based on a position to which the slider is moved.

The scent diffuser may include one or more of the following optional features. The slider includes a plate that is disposed in the holder and that is configured to move along the holder to cover the discharge port; an opening adjustment port in the plate, the opening adjustment port being configured to overlap the discharge port to expose the scent member outward; and the manipulation part is disposed at the plate, the manipulation part being exposed outside of the holder and being configured to transmit the force applied by the user to the plate; where the plate is disposed in the holder such that the plate is configured to move simultaneously with the manipulation part to change an area that covers the discharge port. The holder is provided with a slit configured to guide movement of the manipulation part, and the manipulation part is configured to move along the slit.

The opening adjustment port includes a plurality of opening adjustment ports, and the plurality of opening adjustment ports and the manipulation part are arranged in a line. The slider includes an interference protrusion, the holder includes at least one positioning protrusion configured to interfere with the interference protrusion based on movement of the slider, and an overlapping area between the discharge port and the opening adjustment port is maintained by interference between the positioning protrusion and the interference protrusion. The holder includes a first holder member and a second holder member, the first holder member and the second holder member being configured to rotate relative to each other, the discharge port is located in the first holder member, the scent member is mounted between the first holder member and the second holder member, and the slider is disposed between the scent member and the first holder member.

The first holder member includes a plurality of discharge ports arranged in a line; and a slit that is connected to one of the plurality of discharge ports and that is configured to guide movement of the slider. The manipulation part is inserted through the discharge port and connected to the slit such that the manipulation part is configured to move along the slit. The first holder member includes a movement restriction protrusion configured to restrict a range of movement of the slider. The slider includes an interference protrusion, the holder includes at least one positioning protrusion configured to interfere with the interference protrusion based on movement of the slider, and an overlapping area between the discharge port and the opening adjustment port is maintained by interference between the positioning protrusion and the interference protrusion.

The holder includes a first holder member and a second holder member, the first holder member and the second holder member being configured to rotate relative to each other, a scent member installation space and a slider installation space are defined between the first holder member and the second holder member, the scent member being mounted in the scent member installation space, and the slider being mounted in the slider installation space, the first holder member includes a plurality of discharge ports arranged in a line, and a slit that is connected to one of the plurality of discharge ports and that is configured to guide movement of the slider, and the slider includes a plate disposed in the slider installation space such that the plate is configured to move along the holder to cover the discharge ports, and an opening adjustment port located in the plate, the opening adjustment port being configured to overlap the discharge port to expose the scent member outward, the manipulation part is inserted through the discharge port and connected to the slit such that the manipulation part is exposed outward from the first holder member, the manipulation part being configured to move along the slit based on the user manipulating the manipulation part.

According to another innovative aspect of the subject matter described in this application a clothes treatment apparatus includes a cabinet with a treatment chamber configured to receive clothes and a cycle chamber configured to house machinery; a blowing unit installed in the cycle chamber and configured to circulate air in the treatment chamber; and a scent diffuser separably disposed in the treatment chamber and configured to diffuse scent into the treatment chamber, where the scent diffuser includes a holder configured to hold a replaceable scent member, the holder having at least one discharge port configured to discharge scent emitted from the scent member; and a slider with a manipulation part accessible to a user, the slider being configured to move relative to the holder based on force applied by the user to the manipulation part and the manipulation part being configured to transmit force to the slider, thereby causing the slider to move, where the slider is configured to adjust an extent of an opening of the discharge port based on a position to which the slider is moved.

The scent diffuser may include one or more of the following optional features. The scent diffuser includes a discharge panel defining the treatment chamber, the discharge panel including an air blowing port configured to discharge air blown by the blowing unit, where the scent diffuser is separably mounted in the discharge panel. The scent diffuser is separably mounted in the air blowing port. The scent diffuser includes a steam unit configured to supply steam to the treatment chamber, where the steam unit is mounted in the cycle chamber, and the discharge panel further includes a steam discharge port configured to discharge steam generated by the steam unit.

The holder includes a first holder member and a second holder member, the first holder member and the second holder member being configured to rotate relative to each other, a scent member installation space and a slider installation space are defined between the first holder member and the second holder member, where the scent member is mounted in the scent member installation space, and the slider is mounted in the slider installation space, the first holder member includes a plurality of discharge ports arranged in a line, and a slit that is connected to one of the discharge ports and that is configured to guide movement of the slider, and the slider includes a plate disposed in the slider installation space such that the plate is configured to move along the holder to cover the discharge ports, and an opening adjustment port located in the plate, the opening adjustment port being configured to overlap the discharge port to expose the scent member outward, and the manipulation part is inserted through the discharge port and connected to the slit such that the manipulation part is exposed outward from the first holder member, the manipulation part being configured to move along the slit based on the user manipulating the manipulation part.

The slider includes a plate that is disposed in the holder and that is configured to move along the holder to cover the discharge port; an opening adjustment port located in the plate, the opening adjustment port being configured to overlap the discharge port to expose the scent member outward; and the manipulation part is disposed at the plate, the manipulation part being exposed outside of the holder and being configured to transmit the force applied by the user to the plate, and where the plate is disposed in the holder such that the plate is moved simultaneously with the manipulation part to change an area that covers the discharge port. The opening adjustment port includes a plurality of opening adjustment ports, and the plurality of opening adjustment ports and the manipulation part are arranged in a line. The slider includes an interference protrusion, the holder includes at least one positioning protrusion configured to interfere with the interference protrusion based on movement of the slider, and an overlapping area between the discharge port and the opening adjustment port is maintained by interference between the positioning protrusion and the interference protrusion.

The holder includes a first holder member and a second holder member, the first holder member and the second holder member being configured to rotate relative to each other, the discharge port is located in the first holder member, the scent member is mounted between the first holder member and the second holder member, and the slider is disposed between the scent member and the first holder member. The holder further includes a slider installation space defined in the first holder member, the slider being movably mounted to the slider installation space; and a scent member installation space defined in the second holder member, the replaceable scent member being mounted in the scent member installation space.

BRIEF DESCRIPTION OF THE DRAWINGS

The implementations will be described in detail with reference to the following drawings in which like reference numerals refer to like elements wherein.

DETAILED DESCRIPTION

Figure 1:
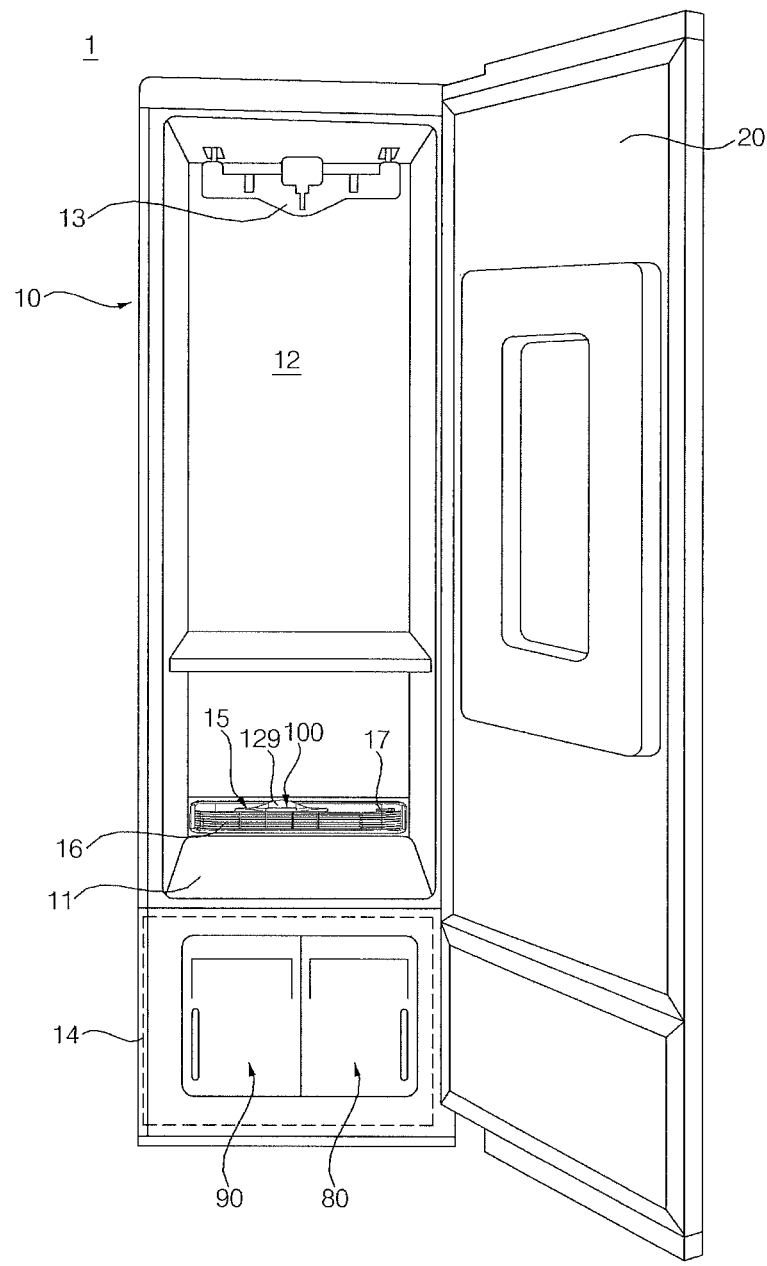
FIG. 1 is a front perspective view of an example clothes treatment apparatus.
Figure 2:
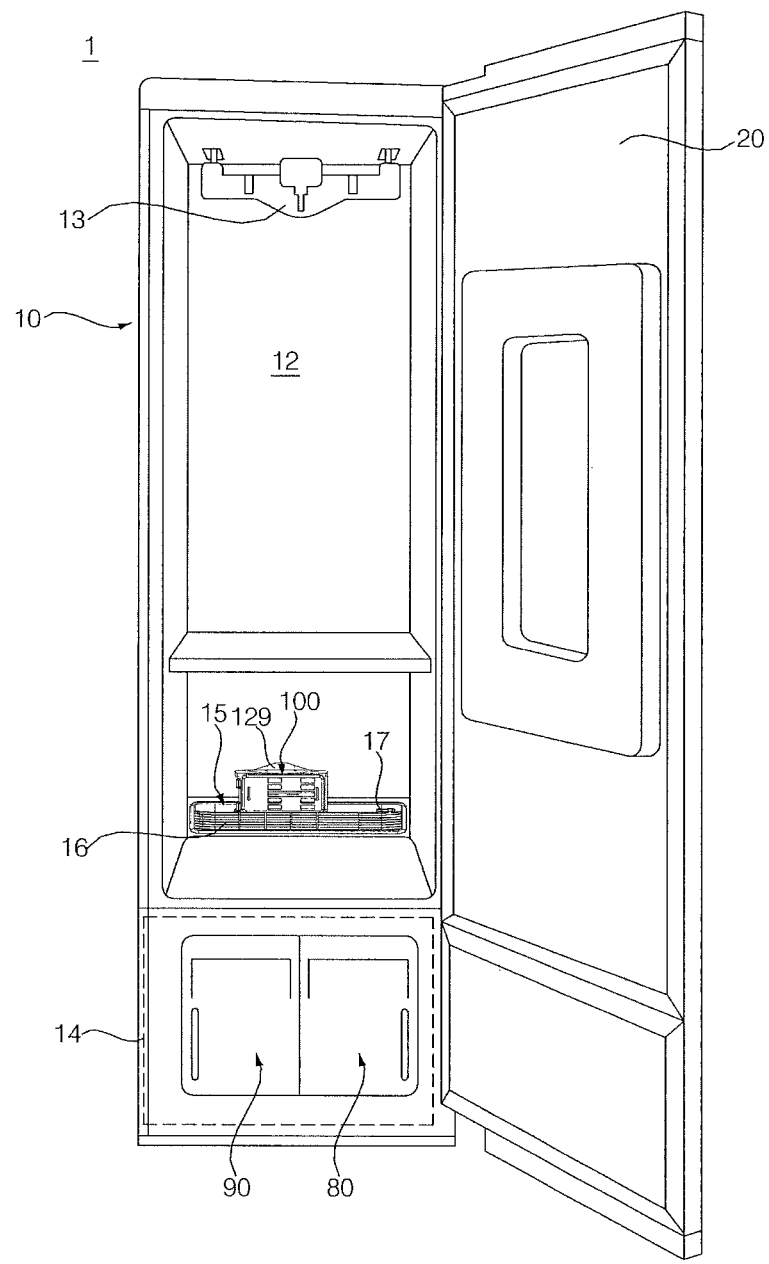
FIG. 2 is a perspective view of an example scent diffuser, which is separated from the clothes treatment apparatus shown in FIG. 1.
Figure 3:
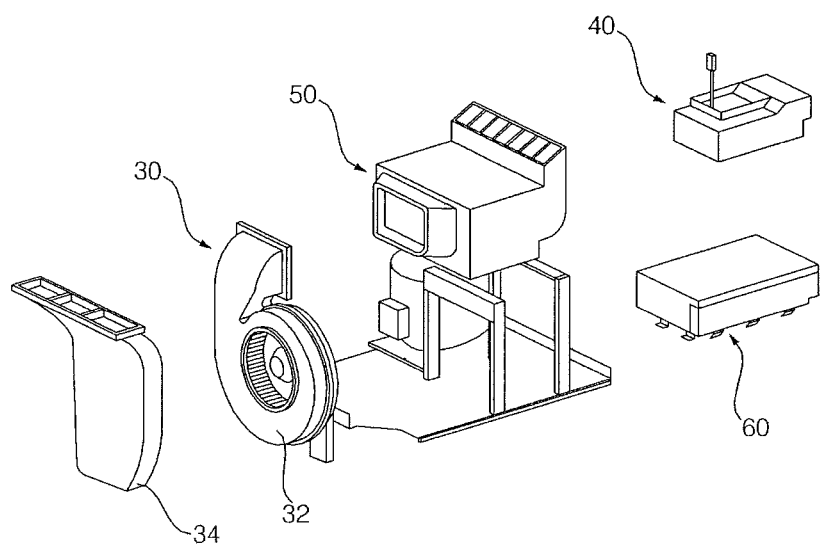
FIG. 3 is an exploded perspective view of an example cycle assembly.
Figure 4:
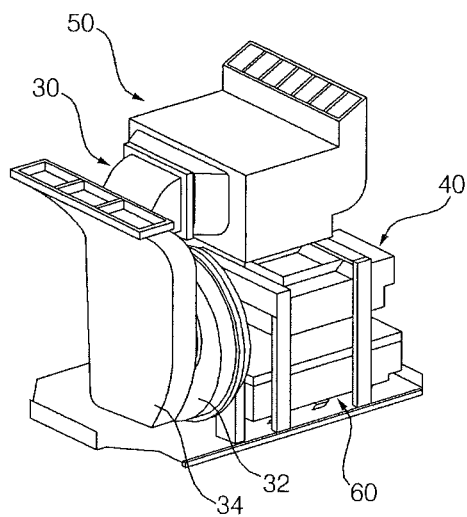
FIG. 4 is a perspective view of the example cycle assembly.
Figure 5:
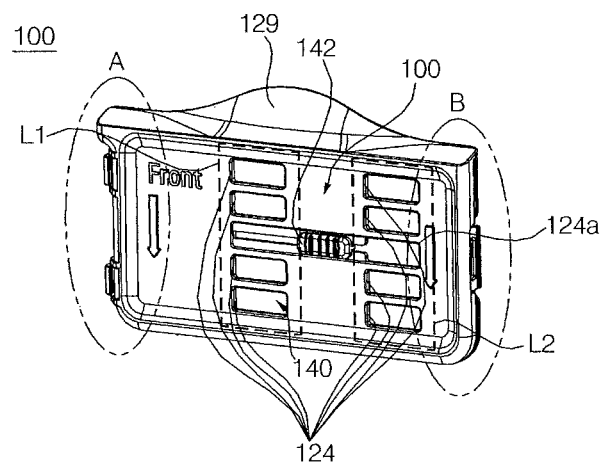
FIG. 5 is a perspective view of the scent diffuser shown in FIG. 2.
Figure 6:
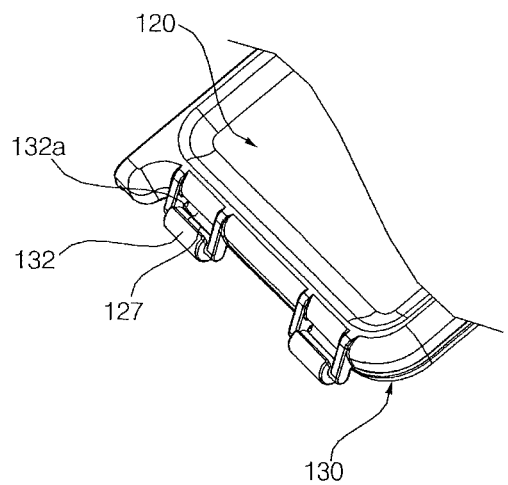
FIG. 6 is a detailed perspective view of part A shown in FIG. 5.
Figure 7:
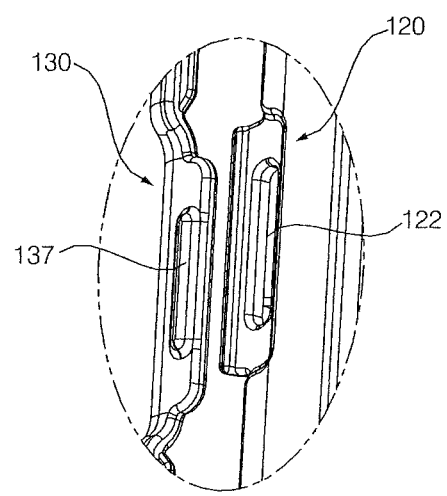
FIG. 7 is a detailed exploded perspective view of part B shown in FIG. 5.

Hereinafter, an example clothes treatment will be described with reference to FIGS. 1 to 4 and 16.

The clothes treatment apparatus 1 according to this implementation includes a cabinet 10, which defines a treatment chamber 12 that is open at the front thereof, and a door 20 configured to open and close the front of the cabinet 10.

The interior of the cabinet 10 is partitioned into upper and lower interior parts by a partition plate 11. A treatment chamber 12, in which clothes are hung, is defined in the interior of the cabinet 10 above the partition plate 11. A cycle chamber 14, in which machinery is installed, is defined in the interior of the cabinet 10 below the partition plate 11.

Clothes may be hung in the treatment chamber 12. In the treatment chamber 12, wrinkles in the clothes may be smoothed, or the clothes may be deodorized, by the circulation of steam or air.

A hanger support bar 13 is configured to support clothes hangers, on which clothes may be hung, is provided in the upper part of the treatment chamber 12. The hanger support bar 13 may be configured to be moved in the treatment chamber 12 in forward and rearward directions, in upward and downward directions, and/or in leftward and rightward directions by a driving device, such as a motor. The hanger support bar 13 may be periodically reciprocated.

An air blowing port 16 and a steam discharge port 17 are formed in the treatment chamber 12.

In this implementation, the air blowing port 16 and the steam discharge port 17 are formed in a discharge panel 15.

The air blowing port 16 and the steam discharge port 17 may be formed in different panels. In this implementation, the discharge panel 15 constitutes a portion of the cycle chamber 14. The discharge panel 15 is located at the rear side of the partition plate 11. The discharge panel 15 and the partition plate 11 form a continuous surface. The discharge panel 15 may be inclined toward the partition plate 11.

Air blown by a blowing unit 30 is discharged through the air blowing port 16.

Steam generated by a steam unit 40 is discharged through the steam discharge port 17.

A blowing unit 30 for circulating air in the treatment chamber 12, a steam unit 40 for supplying steam into the treatment chamber 12, a heat pump unit 50 for conditioning air in the treatment chamber 12, and a control unit 60 for controlling the respective units 30, 40, and 50 may be installed in the cycle chamber 14.

In this implementation, an assembly of machinery, including the blowing unit 30, the steam unit 40, the heat pump unit 50, and the control unit 60, which are required to perform respective cycles of the clothes treatment apparatus, is defined as a cycle assembly.

The blowing unit 30 includes a blowing fan 32 and an inlet duct 34.

The inlet duct 34 is installed at the suction side of the blowing fan 32 to guide air in the treatment chamber 12 to the blowing fan 32.

The blowing fan 32 may be rotated to blow air. The blowing fan 32 suctions air from the treatment chamber 12, and discharges the suctioned air to the heat pump unit 50.

When the steam unit 40 is powered on, heat is generated from the steam unit 40. The steam unit 40 converts water supplied from a water supply tank 80, which will be described hereinafter, into steam. The generated steam may be discharged into the treatment chamber 12.

In this implementation, a flow channel may be defined such that the steam flows into the treatment chamber 12 via the heat pump unit 50.

The heat pump unit 50 may include a heat pump cycle that includes a compressor, a condenser, an evaporator, and an expansion valve. Based on the operation mode of the heat pump unit 50, cooled air or heated air may be discharged into the treatment chamber 12.

In particular, the heat pump unit 50 may heat air around the condenser through heat exchange with a refrigerant, and may supply the heated air into the treatment chamber 12 through the blowing unit 30. The high-temperature air, which may be supplied into the treatment chamber 12, is used to treat clothes that are hung on the clothes hangers, which are supported by the hanger support bar 13. In a case which the heat pump unit 50 is not operated, but only the blowing unit is operated, room-temperature air is supplied into the treatment chamber 12. In addition, air cooled by the evaporator may be supplied into the treatment chamber 12 through the blowing unit 30.

The heat pump unit 50 may dehumidify the air in the treatment chamber 12.

A tank module 70 for storing water may be installed in front of the cycle chamber 14. The tank module 70 may include a water supply tank 80 for supplying water to the steam unit 40 and a drainage tank 90 for collecting and storing condensed water that is generated in the treatment chamber 12.

A water supply level sensor 81 for sensing the level of water stored in the water supply tank 80 is installed in the water supply tank 80, and a drainage level sensor 91 for sensing the level of water stored in the drainage tank 90 is installed in the drainage tank 90.

Water from the water supply tank 80 flows to the steam unit 40 via a water supply pump 45.

Water that is condensed in the treatment chamber 12 flows to the lower side of the treatment chamber 12 due to gravity, and may then be pumped to the drainage tank 90 by a drainage pump 46. Water that is condensed in the heat pump unit 50 also flows to the drainage tank 90 via the drainage pump 46.

The water supply pump 45 or the drainage pump 46 is controlled by the control unit 60.

In this implementation, a tank module frame 71 may be installed in front of the inlet duct 34.

A tank installation space 73 may be defined between the tank module frame 71 and the door 20. The tank module frame 71 may be coupled to the partition plate 11 to isolate the cycle chamber 14 from the outside.

A tank support bar 75, which is configured to interfere with at least one selected from between the water supply tank 80 and the drainage tank 90, may be installed in front of the tank installation space 73.

The tank support bar 75 prevents the water supply tank and/or the drainage tank 90 from being unintentionally separated from the tank installation space 73. The tank support bar 75 is configured to support the front of the water supply tank 80 and the front of the drainage tank 90.

When the door 20 is opened and closed, the water supply tank 80 and the drainage tank 90 are prevented from being separated from the tank installation space 73.

In this implementation, the lower end of the water supply tank 80 may be placed on the upper end of the tank support bar 75, and the lower end of the drainage tank 90 may be placed on the upper end of the tank support bar 75.

A tank support end 79, which is configured to interfere with the tank support bar 75, may be formed on at least one selected from between the water supply tank 80 and the drainage tank 90.

The tank support end 79 may be concavely recessed.

The front of the tank support bar 75 and the front of the water supply tank 80 may be configured to form a continuous surface due to the tank support end 79. In addition, the front of the tank support bar 75 and the front of the drainage tank 90 may be configured to form a continuous surface due to the tank support end 79.

The water supply tank 80 and the drainage tank 90 may be disposed in the tank installation space 73 such that the water supply tank 80 and the drainage tank 90 are arranged parallel to each other in rightward and leftward directions.

When the door 20 is in an opened position, the water supply tank 80 and the drainage tank 90 are exposed to a user.

The water supply tank 80 and the drainage tank 90 may be withdrawn by the user.

The water supply tank 80 and the drainage tank 90 may be separated from the tank module frame 71. The water supply tank 80 and the drainage tank 90 may be separably mounted in the tank installation space 73.

The water supply tank 80 may be connected to the steam unit 40 to supply water to the steam unit 40. The drainage tank 90 may be connected to the treatment chamber 12 to store water discharged from the treatment chamber 12 or the heat pump unit 50.

The drainage tank 90 may be configured to function identical to the water supply tank 80. The drainage tank 90 may be disposed alongside the water supply tank 80.

The clothes treatment apparatus 1 may further include a scent diffuser 100 configured to diffuse scent into the treatment chamber 12. The scent diffuser 100 may be disposed in the treatment chamber 12. After the scent diffuser 100 is completely used, the user may replace the scent diffuser 100 with a new one.

In this implementation, the scent diffuser 100 may be separably mounted in the discharge panel 15. The scent diffuser 100 may be inserted into an opening formed in the discharge panel 15. The user may simply pull the scent diffuser 100 to separate the scent diffuser 100 from the discharge panel 15.

The scent diffuser 100 may be provided with a handle 129. The user may pull the scent diffuser 100 while holding the handle 129 to separate the scent diffuser 100 from the discharge panel 15.

The scent diffuser 100 may be provided in a flow channel along which air blown by the blowing unit 30 is guided to the air blowing port 16. Alternatively, the scent diffuser 100 may be separably provided at any constructional component, such as the door 20, other than the discharge panel 15 as long as the scent diffuser 100 can supply scent into the treatment chamber 12.

Hereinafter, an example scent diffuser 100 will be described in detail with reference to FIGS. 5 to 17.

A replaceable scent member 5 may be mounted in the scent diffuser 100.

The scent diffuser 100 may be separably mounted in the discharge panel 15.

The scent diffuser 100 includes a holder 110, in which the scent member 5 is mounted, the holder 110 having at least one discharge port 124, and a slider 140 movably provided at the holder 110 for adjusting the extent of opening of the discharge port 124 based on the position thereof.

The scent member 5 may be made of a material that diffuses scent. When the scent member 5 is exposed to the air, the scent member 5 diffuses scent into the air. In this implementation, the scent member 5 may be provided in a sheet type form. The scent member 5 may be provided in various other forms, such as a particle type form and a liquid type form.

When the scent member 5 is completely used, the user may separate the scent member 5 from the discharge panel 15 of the treatment chamber 12, and may then mount a new one in the discharge panel 15 of the treatment chamber 12.

The holder 110 may be provided with a scent member installation space 111, in which the scent member 5 is received. Scent discharged from the scent member 5 may be diffused to the outside through the discharge port 124.

A plurality of discharge ports 124 may be provided. In this implementation, the discharge ports 124 constitute a plurality of lines. The discharge ports 124 constitute a plurality of lines in a longitudinal direction.

The discharge ports 124 constitute two lines L1 and L2 (see FIG. 5), which are spaced apart from each other in a direction in which the slider 140 moves. The extents of opening of the discharge ports 124 constituting each line L1 or L2 are simultaneously adjusted by the slider 140.

Hereinafter, the discharge ports 124 constituting the first line L1 will be referred to as first discharge ports, and the discharge ports 124 constituting the second line L2 will be referred to as second discharge ports, as needed.

At least a portion of the slider 140 may be exposed outward from the holder 110 such that the user can manipulate the slider 140. The slider 140 may be moved by a user's manipulation, whereby the extent of opening of the first discharge ports and the second discharge ports may be adjusted.

The holder 110 includes a first holder member 120 and a second holder member 130. The scent member installation space 111, in which the scent member 5 is mounted, may be formed between the first holder member 120 and the second holder member 130.

The scent member installation space 111 may be formed in the first holder member 120 or the second holder member 130. In this example, the scent member installation space 111 may be formed in the second holder member 130. A slider installation space 113, in which the slider 140 is mounted, may be formed in the first holder member 120.

The discharge ports 124 may be formed in the first holder member 120 or the second holder member 130. In this implementation, the discharge ports 124 are formed in the first holder member 120.

The first holder member 120 includes a first housing 121, in which the slider installation space 113 is formed.

The second holder member 130 includes a second housing 131, in which the scent member installation space 111 is formed.

The scent member 5 and the slider 140 are arranged opposite to each other.

The discharge ports 124 and a slit 125 are formed in the first housing 121.

The slit 125 extends in a longitudinal direction of the first holder member 120 to guide the movement of the slider 140.

The slit 125 may be formed separately from the discharge ports 124. In this implementation, the slit 125 may be connected to one of the discharge ports 124, i.e. a discharge port 124a.

In this implementation, the discharge port 124*a* connected to the slit 125 is used as a manipulation part installation hole, in which the slider 140 is mounted. The manipulation part installation hole may be formed separately from the discharge port 124*a*.

The discharge port 124*a* is formed so as to be wider than the slit 125.

The first holder member 120 and the second holder member 130 may be separably coupled to each other. Furthermore, the first holder member 120 and the second holder member 130 may be connected to each other such that the first holder member 120 and the second holder member 130 can be rotated relative to each other.

To this end, one selected from between the first holder member 120 and the second holder member 130 may include a pivot 127, which is used as a rotational shaft about which the other selected from between the first holder member 120 and the second holder member 130 can be rotated, and the other selected from between the first holder member 120 and the second holder member 130 may include a hinge coupling unit 132, which is rotatably coupled to the pivot 127.

The hinge coupling unit 132 may be separably coupled to the pivot 127. The hinge coupling unit 132 extends so as to correspond to the pivot 127.

The hinge coupling unit 132 may be provided with a recess 132*a* (see FIG. 6), through which the pivot 127 is inserted. The hinge coupling unit 132 may be formed from an elastic material (e.g. a synthetic resin) such that the circumference of the recess 132*a* is elastically deformed to some extent when the pivot 127 is inserted into the recess 132*a*. The first holder member 120, the second holder member 130, and/or the slider 140 may be made of a synthetic resin by injection molding.

The pivot 127 may be forcibly inserted into the hinge coupling unit 132. When the pivot 127 is inserted into the hinge coupling unit 132, the hinge coupling unit 132 is elastically deformed such that the pivot 127 can be inserted into the hinge coupling unit 132. When the pivot 127 is separated from the hinge coupling unit 132, the hinge coupling unit 132 may also be elastically deformed.

The slider 140 includes a plate 141 disposed in the holder 110 such that the plate 141 can move along the holder 110. A manipulation part 142 may be formed at the plate 141, the manipulation part 142 being exposed outward from the holder 110. The manipulation part 142 may be manipulated by a user, and is configured to move along the slit 125. The opening adjustment ports 144 may be formed in the plate 141, the opening adjustment ports 144 being configured to overlap the discharge ports 124 so as to expose the scent member 5.

The plate 141 may be disposed in the holder 110 to change the area that covers the discharge ports 124 based on the position of the slider 140.

The manipulation part 142 is the exposed portion of the slider 140, and is exposed outward from the holder 110. The manipulation part 142 constitutes a portion of the slider 140. In this implementation, the manipulation part 142 protrudes from the plate 141. In a case where the holder is configured to have a structure in which a portion of the plate 141 is exposed outward, the exposed portion of the plate 141, which is exposed outward from the holder, may be used as the manipulation part.

The extent of opening the discharge ports 124 may be adjusted based on the area covered by the plate 141. One side part of the plate 141 is configured to adjust the extent of opening of the first discharge ports 124, and the other side part of the plate 141 is configured to adjust the extent of opening of the second discharge ports 124, on the basis of the manipulation part 142.

The slit 125, which extends in a direction in which the manipulation part 142 moves, may be formed in the holder 110. In this case, the manipulation part 142 may move along the slit 125. The slit 125 may extend from one of the discharge ports 124, i.e. the discharge port 124*a*. The discharge port 124*a*, which is connected to the slit 125, is sufficiently large to allow the manipulation part 142 to pass therethrough.

The manipulation part 142 may be inserted into the discharge port 124*a* from the inside of the discharge port 124*a* such that the manipulation part 142 protrudes outward from the first holder member 120.

The slit 125 is formed so as to be narrower than each of the discharge ports 124. The slit 125 extends in a direction in which the slider 140 moves. The manipulation part 142 is connected to the plate 141 via a connection part that is narrow enough to pass through the slit 125.

The amount of scent discharged from the scent diffuser 100 may be set based on the extent of opening of the discharge ports 124. The extent of opening of the discharge ports 124 corresponds to the position of the manipulation part 142.

The plate 141 is configured to move to adjust the area of the discharge ports 124 that is covered. Referring to FIGS. 10 to 17, it can be seen that the extent of opening of the discharge ports 124 can be adjusted through several stages based on the position of the manipulation part 142.

In the slider 140, the manipulation part 142 may be located at the middle of the opening adjustment ports 144. The opening adjustment ports 144 disposed at the upper side of the manipulation part 142 and the opening adjustment ports 144 disposed at the lower side of the manipulation part 142 may be arranged symmetrically.

The slit 125 may be located in the middle of the holder 110. The manipulation part 142 is configured to move along the slit 125, which is located in the middle of the holder 110. The user may intuitively check the position of the manipulation part 142.

A plurality of opening adjustment ports 144 is provided. The opening adjustment ports 144 simultaneously overlap the discharge ports 124 constituting the first line L1 or the discharge ports 124 constituting the second line L2.

For example, the opening adjustment ports 144 may simultaneously adjust the extent of opening of the discharge ports 124 constituting the first line L1. The scent member 5 may be exposed from the discharge ports 124 through the opening adjustment ports 144.

In this implementation, one opening adjustment port 144 overlaps one discharge port 124.

The opening adjustment ports 144 and the manipulation part 142 are arranged in a line.

The opening adjustment ports 144 move the same distance as the manipulation part 142.

In the above arrangement, it is possible for the user to intuitively check the extent of opening of the discharge ports 124. The extent of opening of the discharge ports 124 is adjusted based on the position of the manipulation part 142.

When the manipulation part 142 is completely aligned with the discharge ports 124, the discharge ports 124 are completely open. On the other hand, when the manipulation part 142 completely deviates from the discharge ports 124, the discharge ports 124 are completely closed.

The slider 140 may be provided with at least one interference protrusion 143.

The holder 110 may be provided with one or more positioning protrusions 126a to 126f, which are located in a path along which the interference protrusion 143 moves and which interfere with the interference protrusion 143 when the slider 140 is moved.

The number of positioning protrusions 126a to 126f may be greater than the number of interference protrusions 143. When the user moves the manipulation part 142, the user may perceive the sensation of the interference protrusions 143 moving over the positioning protrusions 126a to 126f.

Since the positions of the positioning protrusions 126a to 126f are set so as to correspond to the extent of opening of the discharge ports 124, the user may manipulate the slider 140 such that the slider 140 can be appropriately positioned based on a predetermined extent of opening of the discharge ports 124.

The holder 110 may be provided with at least one movement restriction protrusion 128a and 128b for limiting a movable range of the slider 140. The slider 140 may be disposed between the movement restriction protrusion 128a and 128b.

The movement of the slider 140 in one direction may be restricted by the first movement restriction protrusion 128a, and the movement of the slider 140 in the other direction is restricted by the second movement restriction protrusion 128b.

The discharge ports 124 may be completely closed (see FIG. 10 or 11) at a position at which the slider 140 cannot move any further due to the first movement restriction protrusion 128a. The discharge ports 124 may be completely open (see FIG. 16 or 17) at a position at which the slider 140 cannot move any further due to the second movement restriction protrusion 128b.

The movement restriction protrusions 128a and 128b are formed in a direction crossing the movement path of the slider 140. In this implementation, each of the movement restriction protrusions 128a and 128b may be formed to have a rib shape.

Figure 8:
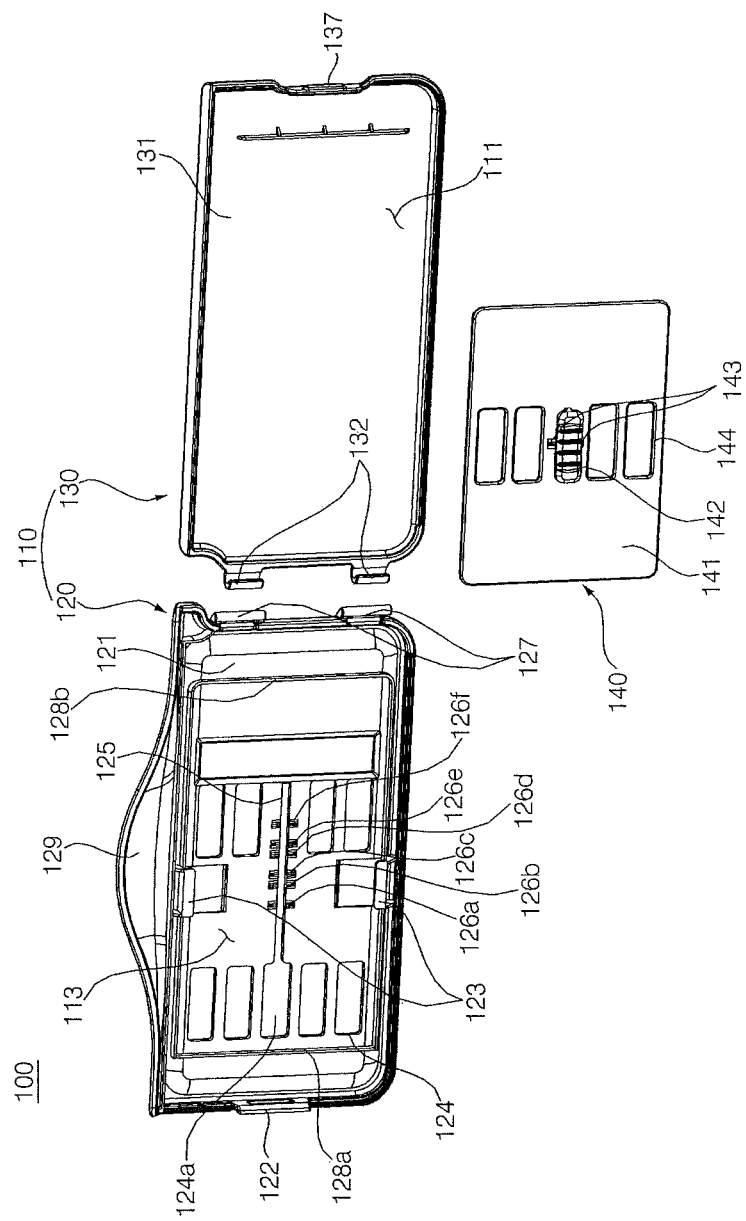
FIG. 8 is an exploded perspective view of the scent diffuser shown in FIG. 5.
Figure 9:
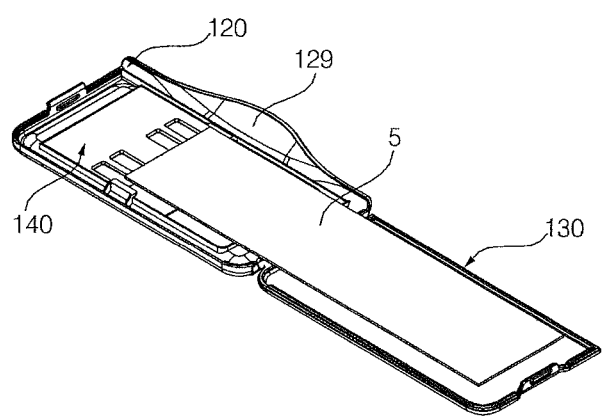
FIG. 9 is a perspective view of the scent diffuser shown in FIG. 5 in a state in which the scent diffuser is open.

Referring to FIG. 8, the interference protrusions 143 may be provided at opposite sides of the manipulation part 142. In the first housing 121, positioning protrusions 126a to 126f for restricting the position of one interference protrusion 143 may be disposed at one side of the slit 125 such that the positioning protrusions 126a to 126f are arranged in a line.

In the first housing 121, positioning protrusions 126a to 126f for restricting the position of the other interference protrusion 143 may be disposed at the other side of the slit 125, such that the positioning protrusions 126a to 126f are arranged in a line. The positioning protrusions 126a to 126f for restricting the position of one interference protrusion 143 and the positioning protrusions 126a to 126f for restricting the position of the other interference protrusion 143 may be disposed symmetrically.

Referring to FIGS. 10 to 17, the scent diffuser 100 may be configured such that the discharge ports 124 can be adjusted to have four extents of opening, for example, fully open, ⅓ open, ⅔ open, and fully closed. The six positioning protrusions 126a to 126f may be arranged along the movement path of the interference protrusions 143 in a line.

Figure 10:
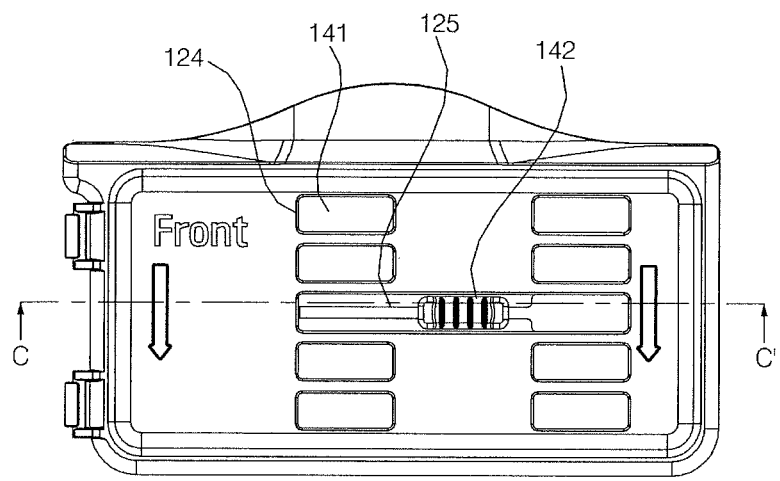
FIG. 10 is a view showing a first example of the operation of the scent diffuser shown in FIG. 5 when a discharge port of the scent diffuser is completely closed.
Figure 11:
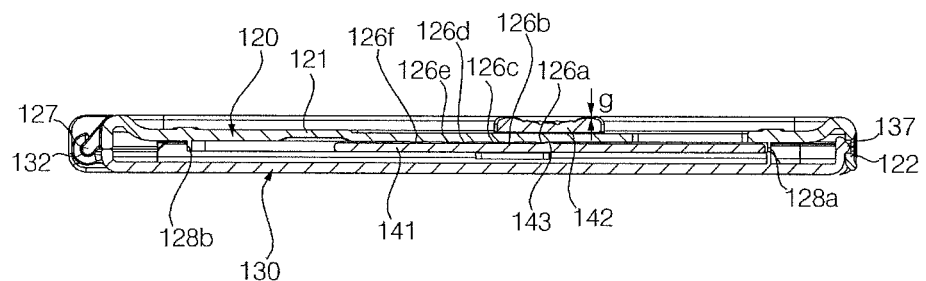
FIG. 11 is a sectional view taken along line C-C' of FIG. 10.

Referring to FIG. 10 or 11, the first positioning protrusion 126a is configured to interfere with the interference protrusion 143 when the slider 140 is moved from the left to the right. After the interference protrusion 143 moves over the first positioning protrusion 126a, the slider 140 comes into contact with the first positioning protrusion 126a, with the result that the slider 140 does not move any further.

Figure 12:
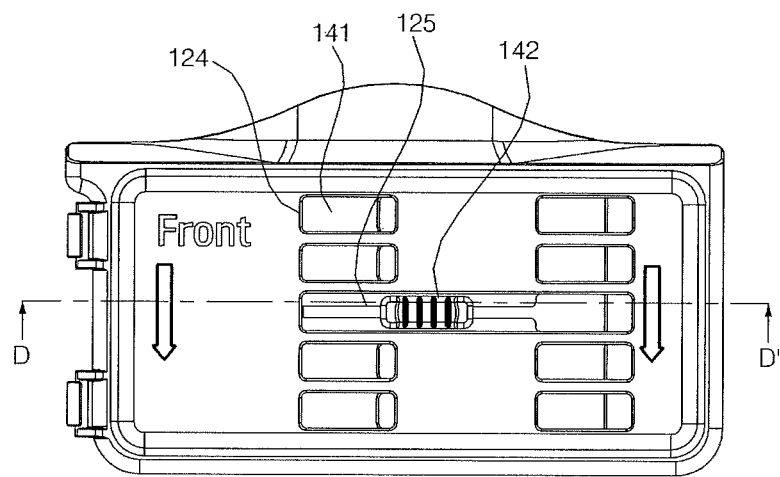
FIG. 12 is a view showing a second example of the operation of the scent diffuser shown in FIG. 10 when the discharge port of the scent diffuser is ⅓ open.
Figure 13:
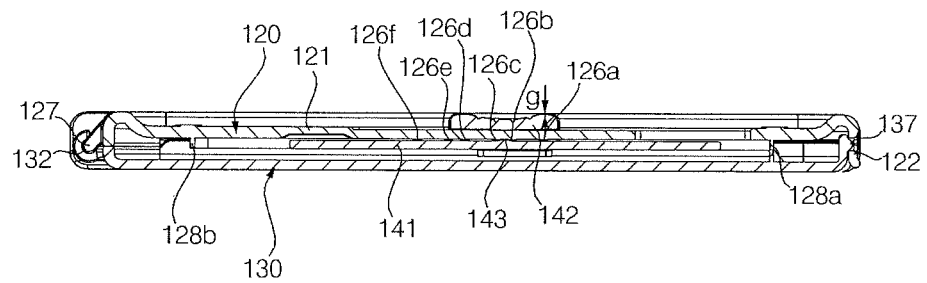
FIG. 13 is a sectional view taken along line D-D' of FIG. 12.

Referring to FIG. 12 or 13, the second positioning protrusion 126b and the third positioning protrusion 126c are provided so as to set the position of the slider 140 at which the discharge ports 124 are ⅓ open.

In a state in which the discharge ports 124 are ⅓ open, the interference protrusion 143 is located between the second positioning protrusion 126b and the third positioning protrusion 126c (hereinafter, referred to as a ⅓ open position).

Figure 14:
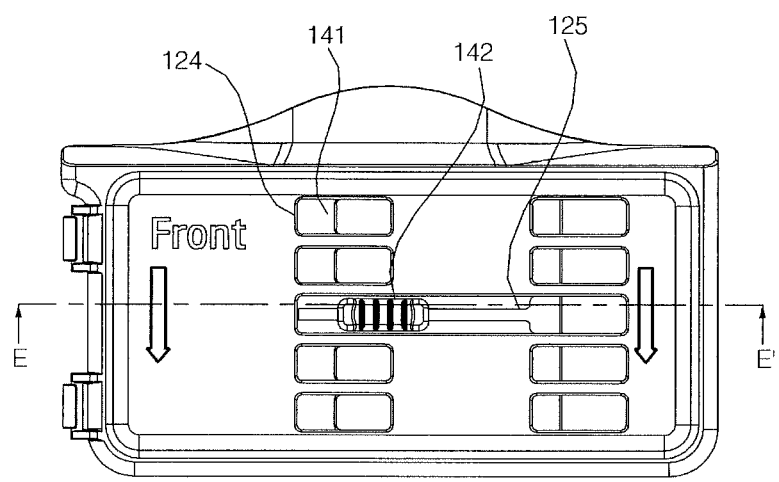
FIG. 14 is a view showing a third example of the operation of the scent diffuser shown in FIG. 10 when the discharge port of the scent diffuser is ⅔ open.
Figure 15:
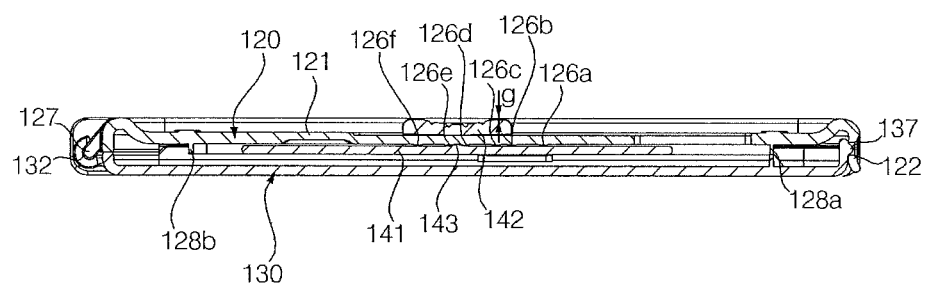
FIG. 15 is a sectional view taken along line E-E' of FIG. 14.

Referring to FIG. 14 or 15, the fourth positioning protrusion 126d and the fifth positioning protrusion 126e are provided so as to correspond to the position of the slider 140 at which the discharge ports 124 are ⅔ open.

In a state in which the discharge ports 124 are ⅔ open, the interference protrusion 143 is located between the fourth positioning protrusion 126d and the fifth positioning protrusion 126e (hereinafter, referred to as a ⅔ open position).

Figure 16:
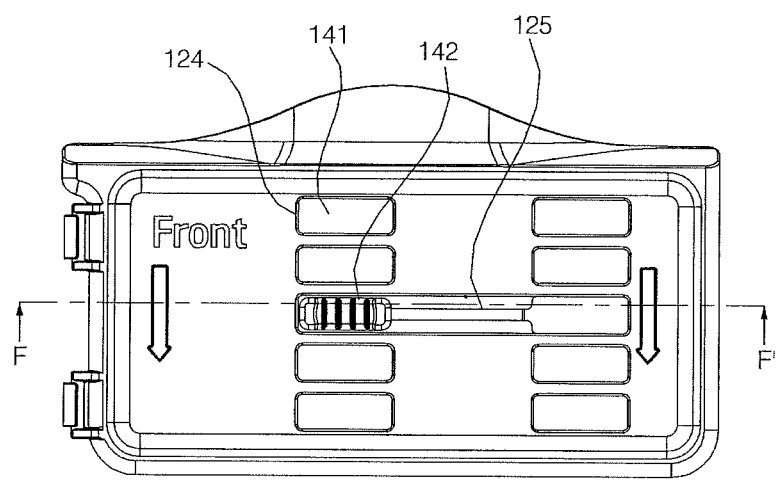
FIG. 16 is a view showing a fourth example of the operation of the scent diffuser shown in FIG. 10 when the discharge port of the scent diffuser is completely open.
Figure 17:
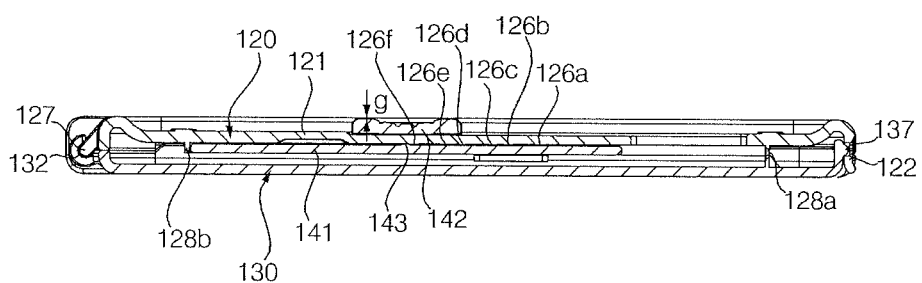
FIG. 17 is a sectional view taken along line F-F' of FIG. 16.
Figure 18:
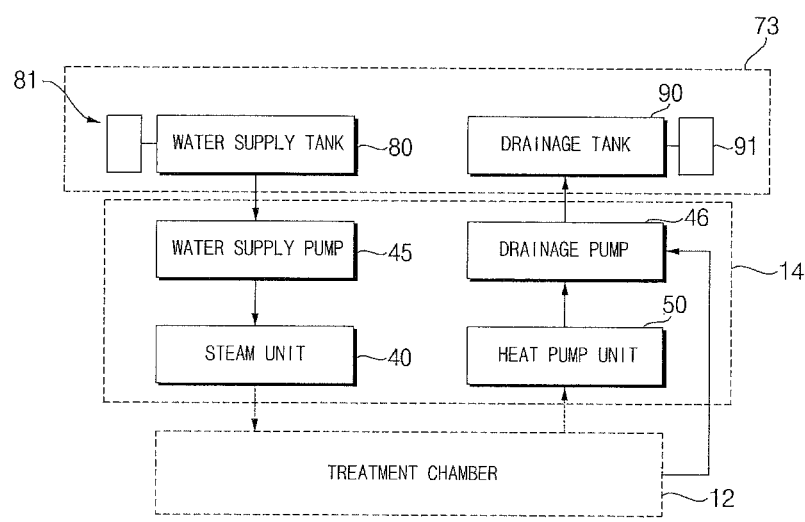
FIG. 18 is a block diagram of an example clothes treatment apparatus.

Referring to FIG. 16 or 17, when the slider 140 is moved from the position at which the discharge ports 124 are ⅔ open, the interference protrusion 143 moves over the six positioning protrusion 126f. At this time, the slider 140 comes into contact with the second movement restriction protrusion 128b, with the result that the slider 140 does not move any further.

As described above, the positioning protrusions 126a to 126f may enable the user to recognize the positions of the slider 140 that correspond to the extent of opening of the discharge ports 124 based on the sensation of manipulation during the manipulation of the slider 140, and may prevent the movement of the slider 140 after the interference protrusions 143 are located at the predetermined positions (e.g. the ⅓ open position and the ⅔ open position).

According to implementations, the positioning protrusions may be configured differently. For example, a larger number of positioning protrusions may be provided in order to adjust the extent of opening of the discharge ports 124 through a larger number of stages.

In another implementation, one selected from between the slider 140 and the holder 110 may include an interference protrusion, and the other selected from between the slider 140 and the holder 110 may include positioning insertion parts, into which the interference protrusion is inserted when the slider 140 is located at predetermined positions. In this case, the positioning insertion parts may be provided at positions corresponding to the extent of opening of the discharge ports 124 and the interference protrusion may be inserted into the positioning insertion parts during the movement of the slider 140.

It will be apparent that, although implementations have been described above with reference to the accompanying drawings, the disclosure is not limited to the above-described implementations, and therefore various modifications and variations can be made by those skilled in the art without departing from the scope of the appended claims. Thus, modifications and variations should not be understood independently of the technical spirit or prospect of the disclosure. The above implementations are therefore to be construed in all aspects as illustrative and not restrictive.

What is claimed is:

1. A scent diffuser comprising:
    a holder configured to hold a replaceable scent member, the holder having at least one discharge port configured to discharge scent emitted from the scent member; and
    a slider with a manipulation part accessible to a user, the slider being configured to move relative to the holder based on force applied by the user to the manipulation part, and the manipulation part being configured to transmit force to the slider, thereby causing the slider to move, wherein the slider is configured to adjust an extent of an opening of the discharge port based on a position to which the slider is moved, wherein:

the holder comprises a first holder member and a second holder member, the first holder member and the second holder member being configured to rotate relative to each other, a scent member installation space and a slider installation space are defined between the first holder member and the second holder member, the scent member being mounted in the scent member installation space, and the slider being mounted in the slider installation space, the first holder member comprises a plurality of discharge ports arranged in a line, and a slit that is connected to one of the plurality of discharge ports and that is configured to guide movement of the slider, and the slider comprises:
a plate disposed in the slider installation space such that the plate is configured to move along the holder to cover the discharge ports, and
an opening adjustment port located in the plate, the opening adjustment port being configured to overlap the discharge port to expose the scent member outward, the manipulation part is inserted through the discharge port and connected to the slit such that the manipulation part is exposed outward from the first holder member, the manipulation part being configured to move along the slit based on the user manipulating the manipulation part.

2. The scent diffuser according to claim 1, wherein the plate is disposed in the holder such that the plate is configured to move simultaneously with the manipulation part to change an area that covers the discharge port.

3. The scent diffuser according to claim 1, wherein the opening adjustment port comprises a plurality of opening adjustment ports, and the plurality of opening adjustment ports and the manipulation part are arranged in a line.

4. The scent diffuser according to claim 1, wherein:
the slider includes an interference protrusion,
the holder comprises at least one positioning protrusion configured to interfere with the interference protrusion based on movement of the slider, and
an overlapping area between the discharge port and the opening adjustment port is maintained by interference between the positioning protrusion and the interference protrusion.

5. The scent diffuser according to claim 1, wherein:
the first holder member and the second holder member being configured to rotate relative to each other,
the discharge port is located in the first holder member,
the scent member is mounted between the first holder member and the second holder member, and
the slider is disposed between the scent member and the first holder member.

6. The scent diffuser according to claim 1, wherein the first holder member includes a movement restriction protrusion configured to restrict a range of movement of the slider.

7. The scent diffuser according to claim 1, wherein:
the slider includes an interference protrusion,
the holder comprises at least one positioning protrusion configured to interfere with the interference protrusion based on movement of the slider, and
an overlapping area between the discharge port and the opening adjustment port is maintained by interference between the positioning protrusion and the interference protrusion.

8. A clothes treatment apparatus comprising:
a cabinet with a treatment chamber configured to receive clothes and a cycle chamber configured to house machinery;
a blowing unit installed in the cycle chamber and configured to circulate air in the treatment chamber; and
a scent diffuser separably disposed in the treatment chamber and configured to diffuse scent into the treatment chamber, wherein the scent diffuser comprises:
a holder configured to hold a replaceable scent member, the holder having at least one discharge port configured to discharge scent emitted from the scent member; and
a slider with a manipulation part accessible to a user, the slider being configured to move relative to the holder based on force applied by the user to the manipulation part, and the manipulation part being configured to transmit force to the slider, thereby causing the slider to move,
wherein the slider is configured to adjust an extent of an opening of the discharge port based on a position to which the slider is moved, wherein:

the holder comprises a first holder member and a second holder member, the first holder member and the second holder member being configured to rotate relative to each other, a scent member installation space and a slider installation space are defined between the first holder member and the second holder member, the scent member being mounted in the scent member installation space, and the slider being mounted in the slider installation space, the first holder member comprises a plurality of discharge ports arranged in a line, and a slit that is connected to one of the plurality of discharge ports and that is configured to guide movement of the slider, and the slider comprises:
a plate disposed in the slider installation space such that the plate is configured to move along the holder to cover the discharge ports, and
an opening adjustment port located in the plate, the opening adjustment port being configured to overlap the discharge port to expose the scent member outward, the manipulation part is inserted through the discharge port and connected to the slit such that the manipulation part is exposed outward from the first holder member, the manipulation part being configured to move along the slit based on the user manipulating the manipulation part.

9. The clothes treatment apparatus according to claim 8, further comprising:
a discharge panel defining the treatment chamber, the discharge panel including an air blowing port configured to discharge air blown by the blowing unit, wherein the scent diffuser is separably mounted in the discharge panel.

10. The clothes treatment apparatus according to claim 9, wherein the scent diffuser is separably mounted in the air blowing port.

11. The clothes treatment apparatus according to claim 9, further comprising:
a steam unit configured to supply steam to the treatment chamber, wherein
the steam unit is mounted in the cycle chamber, and
the discharge panel further comprises a steam discharge port configured to discharge steam generated by the steam unit.

12. The clothes treatment apparatus according to claim 8, wherein the opening adjustment port comprises a plurality of opening adjustment ports, and the plurality of opening adjustment ports and the manipulation part are arranged in a line.

13. The clothes treatment apparatus according to claim 8, wherein
the slider includes an interference protrusion,
the holder comprises at least one positioning protrusion configured to interfere with the interference protrusion based on movement of the slider, and
an overlapping area between the discharge port and the opening adjustment port is maintained by interference between the positioning protrusion and the interference protrusion.

14. The clothes treatment apparatus according to claim 8, wherein
the discharge port is located in the first holder member,
the scent member is mounted between the first holder member and the second holder member, and
the slider is disposed between the scent member and the first holder member.

15. The clothes treatment apparatus according to claim 14, wherein the holder further comprises:
a slider installation space defined in the first holder member, the slider being movably mounted to the slider installation space; and
a scent member installation space defined in the second holder member, the replaceable scent member being mounted in the scent member installation space.

* * * * *